(12) United States Patent
Benhadji et al.

(10) Patent No.: US 11,376,259 B2
(45) Date of Patent: Jul. 5, 2022

(54) TARGETED TREATMENT OF MATURE T-CELL LYMPHOMA

(71) Applicant: Eli Lilly and Company, Indianapolis, IN (US)

(72) Inventors: Karim Adnane Benhadji, Green Villiage, NJ (US); Gerard Joseph Oakley, III, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 6 days.

(21) Appl. No.: 16/340,675

(22) PCT Filed: Oct. 6, 2017

(86) PCT No.: PCT/US2017/055650
§ 371 (c)(1),
(2) Date: Apr. 9, 2019

(87) PCT Pub. No.: WO2018/071307
PCT Pub. Date: Apr. 19, 2018

(65) Prior Publication Data
US 2019/0231794 A1 Aug. 1, 2019

Related U.S. Application Data

(60) Provisional application No. 62/407,111, filed on Oct. 12, 2016.

(51) Int. Cl.
*A61K 31/55* (2006.01)
*A61P 35/00* (2006.01)

(52) U.S. Cl.
CPC ............... *A61K 31/55* (2013.01); *A61P 35/00* (2018.01)

(58) Field of Classification Search
CPC ................................ A61K 31/55; A61P 35/00
See application file for complete search history.

(56) References Cited

U.S. PATENT DOCUMENTS

| | | | |
|---|---|---|---|
| 8,569,286 | B2 | 10/2013 | Hipskind et al. |
| 10,555,951 | B2 | 2/2020 | Benhadji |
| 10,688,104 | B2 | 6/2020 | Bender et al. |
| 2005/0187179 | A1 | 8/2005 | Miele et al. |
| 2012/0213029 | A1 | 8/2012 | Villiger |
| 2013/0029972 | A1 | 1/2013 | Hipskind |
| 2018/0104254 | A1 | 4/2018 | Karim et al. |
| 2019/0192531 | A1 | 6/2019 | Bender et al. |
| 2019/0209581 | A1 | 7/2019 | Benhadji et al. |
| 2020/0289565 | A1 | 9/2020 | Green et al. |
| 2022/0008432 | A1 | 1/2022 | Bender et al. |

FOREIGN PATENT DOCUMENTS

| | | |
|---|---|---|
| CN | 101 248 098 | 8/2008 |
| CN | 102 085 372 | 6/2011 |
| CN | 102 264 725 | 11/2011 |
| CN | 103 282 364 | 9/2013 |
| WO | WO 1998/028268 | 7/1998 |
| WO | WO 2007/004743 | 1/2007 |
| WO | WO 2007/005874 | 1/2007 |
| WO | WO 2008/112249 | 9/2008 |
| WO | WO 2008/121742 | 10/2008 |
| WO | WO 2009/023453 | 2/2009 |
| WO | WO 2010/075074 | 7/2010 |
| WO | WO 2011/060051 | 5/2011 |
| WO | WO 2012/097039 | 7/2012 |
| WO | WO 2013/016081 | 1/2013 |
| WO | WO 2014/193898 | 12/2014 |
| WO | WO 2015/026634 | 2/2015 |
| WO | WO 2015/193352 | 12/2015 |
| WO | WO 2016/040880 | 3/2016 |
| WO | WO 2016/164580 | 10/2016 |
| WO | WO 2016/168014 | 10/2016 |
| WO | WO 2017/019496 | 2/2017 |
| WO | WO 2017/180385 | 10/2017 |
| WO | WO 2017/180389 | 10/2017 |
| WO | WO 2017/200969 | 11/2017 |
| WO | WO 2018/044662 | 3/2018 |
| WO | WO 2018/201056 | 11/2018 |
| WO | WO 2019/090364 | 5/2019 |

OTHER PUBLICATIONS

U.S. Appl. No. 16/093,123, filed Oct. 11, 2018, by Beckmann et al. (Copy not submitted herewith pursuant to the waiver of 37 C.F. R. § 1.98(a)(2)(iii) issued by the Office on Sep. 21, 2004).
"Chemotherapy of Neoplastic Diseases," in Goodmann & Gilman's Manual of Pharmacology and Therapeutics (2008) Chapter 51.
Anonymous, "FS25 Peripheral T-Cell Lymphoma Facts I p. 1 Revised," Leukemia & Lymphoma Society (2014) Retrieved on https://www.lls.org/sites/default/files/file_assets/peripheraltcell-lymphomafacts.pdf.
Anonymous, "Notch Inhibitor Shows Modest Efficacy," Cancer Discovery (2016) pp. 1-3. Retrieved on URL:http://cancerdiscovery.aacrjournals.org/content/early/2016/12/13/2159-8290.CD-NB2016-159.
Bender et al., "Novel inhibitor of Notch signaling for the treatment of cancer" (2013) Cancer Res 73(8 Supplement):1131.
Cheson et al., "Revised response criteria for malignant lymphoma.," J Clin. Oncol., K2007) 25(5): 579-586.
Choi et al., "Correlation of computed tomography and positron emission tomography in patients with metastatic gastrointestinal stromal tumor treated at a single institution with imatinib mesylate: proposal of new computed tomography response criteria," J. Clin. Oncol., (2007) 25(13): 1753-1759.
Clinical Trial Identifier NCT/02079636. Updated Feb. 3, 2016. Retrieved from https://clinicaltrials.gov/archive/NCT02079636/2016_02_03.

(Continued)

*Primary Examiner* — Shobha Kantamneni
(74) *Attorney, Agent, or Firm* — Morrison & Foerster LLP

(57) ABSTRACT

A method and medicament comprising 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof for treating aggressive peripheral T-cell lymphoma is provided.

14 Claims, No Drawings

(56) References Cited

OTHER PUBLICATIONS

Clinical Trial Identifier NCT02784795. "A Study of LY3039478 in Participants with Advanced or Metastatic Solid Tumors". Updated May 26, 2016. Retrieved from https://clinicaltrials.gov/archive/NCT02784795/2016_05_26.

Cullion et al., "Targeting the Notch1 and mTOR pathways in a mouse T-ALL model," Blood (2009) 113:6172-6181.

Database WPI, Week 201156, Thomas Scientific, London, GB; AN 2011-J01934, XP002771616, CN 102 085 372 (Inst Basic Medical Sci Chinese Acad Medi), Jun. 8, 2011 abstract.

Eisenhauer et al., "New response evaluation criteria in solid tumours: revised RECIST guideline (version 1.1)," European Journal of Cancer, (2009) 45: 228-247.

Gast et al., "Somatic alterations in the melanoma genome: A high-resolution array-based comparative genomic hybridization study," Genes, Chromosomes & Cancer, (2010) 49: 733-745.

Grabher et al., "Notch 1 activation in the molecular pathogenesis of T-cell acute lymphoblastic leukaemia," Nature Review Cancer, (2006) (6):347-359.

Guijarro et al., "Dual Pten/Tp53 Suppression Promotes Sarcoma Progression by Activating Notch Signaling," Am J Pathol (2013) 182(6):2015-2027.

Hill et al., "Gamma secretase inhibition increase recognition of multiple myeloma by BCMA-specific chimeric antigen receptor modified T cells," J Immunotherapy of Cancer (2017) 5(S2):5-6.

Lipson et al., "Durable Cancer Regression Off-treatment and Effective Reinduction Therapy with an Anti-PD-1 Antibody," Clin Cancer Res (2013) 19(2):462-468.

Massard et al., "First-in-human study of LY3039478, a Notch signaling inhibitor in advanced or metastatic cancer," J Clin Oncol (2015) 33(15_suppl):2533.

Oken et al., "Toxicity and response criteria of the Eastern Cooperative Oncology Group," Am. J. Clin. Oncol., (1982) 5: 649-655.

Pardoll, "The blockade of immune checkpoints in cancer immunotherapy," Nature (2012) 12:252-264.

Park et al., "Notch3 Gene Amplification in Ovarian Cancer," Cancer Research, (2006) 66: 6312-6318.

Ranganathan et al., "Notch signalling in solid tumours: a little bit of everything but not all the time," Nature Review Cancer, (2011) 11:338-351.

Shih et al., "Notch Signaling, γ-Secretase Inhibitors, and Cancer Therapy," Cancer Research, (2007) 67(5):1879-1882.

Smith et al., "A phase I dose escalation and expansion study of the anticancer stem cell agent demcizumab (Anti-DLL4) in patients with previously treated solid tumors," Clin Cancer Re (2014) 20(24):6295-303.

Takebe et al., "Targeting Notch signaling pathway in cancer: Clinical development advances and challenges," Pharmacol Ther (2014) 141(2):140-149.

Tejada et al., "The challenge of targeting Notch in hematologic malignancies," Frontiers in Pediatrics (2014) 2:1-8.

Weng et al., "Activating mutations of NOTCH1 in human T cell acute lymphoblastic leukemia," Science, (2004) 306(5694):269-271.

Westhoff et al., "Alterations of the Notch pathway in lung cancer," PNAS, (2009) 106: 22293-22298.

Worcester, "GSI inhibition may boost BCMA CAR T-cell therapy efficacy in myeloma," Hematology News. Published on Nov. 27, 2017. Retrieved on https://www.mdedge.com/hematology-oncology/article/152733/multiple-myeloma/gsi-inhibition-may-boost-bcma-car-t-cell-therapy.

Young et al., "Measurement of clinical and subclinical tumour response using [18F]-fluorodeoxyglucose and positron emission tomography: review and 1999 EORTC recommendations. European Organization for Research and Treatment of Cancer (EORTC) PET Study Group," Eur J Cancer (1999) 35(13): 1773-82.

Yuen et al., "Abstract CT048: Population pharmacokinetics and pharmacodynamics for an oral Notch inhibitor, LY3039478, in the first-in-man study," Cancer Research (2016) 76(14):CT048.

U.S. Appl. No. 16/093,117, filed Oct. 11, 2018, by Patel et al. (Copy not submitted herewith pursuant to the waiver of 37 C.F. R. § 1.98(a)(2)(iii) issued by the Office on Sep. 21, 2004).

U.S. Appl. No. 16/761,770, filed Nov. 6, 2018, by Green et al. (Copy not submitted herewith pursuant to the waiver of 37 C.F. R. § 1.98(a)(2)(iii) issued by the Office on Sep. 21, 2004).

Martin-Liberal, "Leiomyosarcoma: Principles of management, intractable & rare disease research," (2013) 2(4):127-129.

Mathieu et al., "Notch signaling regulates PD-1 expression during CD8+ T-cell activation," Immunology and Cell Biology, (2013) 91: 82-88.

Wooldridge et al., "Corticosteroids in Advanced Cancer," Oncology (2001) 15 (2):225-236.

U.S. Appl. No. 16/870,853, filed May 8, 2020, by Bender et al. (Copy not submitted herewith pursuant to the waiver of 37 C.F. R. § 1.98(a)(2)(iii) issued by the Office on Sep. 21, 2004).

Gadducci et al., "Pharmacological treatment for uterine leiomyosarcomas", Expert Opin Pharmacother (2014) 16(3):335-346.

Kandoth et al., "Mutational landscape and significance across 12 major cancer types," Nature (2013) 502(7471):333-339.

Lewis et al., "Catalytic site-directed gamma-secretase complex inhibitors do not discriminate pharmacologically between Notch S3 and beta-APP cleavages," Biochemistry (2003) 42(24):7580-7586.

Sahebjam et al., "A Phase I study of the combination of ro4929097 and cediranib in patients with advanced solid tumors (PJC-004/NCI 8503)" Brit J of Cancer (2013) 109:943-949.

Seow et al., "Advances in Targeted and Immunobased Therapies for Colorectal Cancer in the Genomic Era," Onco Targets Ther. (2016) 9: 1899-1920.

Shepard et al., "PI3K/mTOR inhibition upregulates NOTCH-MYC signalling leading to an impaired cytotoxic response," Leukemia (2013) 27:650-660.

Pant et al., Journal of Clinical Oncology, 2012; 30(15_suppl):3008-3008) (Year: 2012).

VanArsdale et al., "Molecular Pathways: Targeting the Cyclin D-CDK4/6 Axis for Cancer Treatment," Clinical Cancer Research, 2015 , 21, 2905-2910.

Laurent et al., "γ-Secretase directly sheds the survival receptor BCMA from plasma cells," Nat Commun (2015) 6:7333.

TARGETED TREATMENT OF MATURE T-CELL LYMPHOMA

CROSS REFERENCE TO RELATED APPLICATIONS

This application is a national stage application under 35 U.S.C. § 371 of International Application No. PCT/US2017/055650, filed internationally on Oct. 6, 2017 which claims the benefit of priority to U.S. provisional patent application No. 62/407,111, filed Oct. 12, 2016, the contents of which are hereby incorporated by reference in their entirety for all purposes.

Mature T-cell lymphoma (more frequently called peripheral T-cell lymphoma; PTCL) is a group of rare and usually aggressive non-Hodgkin lymphomas that develop from mature T lymphocytes. Cancerous T lymphocytes travel to various parts of the body through the lymphatic system, although not confined to the lymphatic system, and form a solid tumor. PTCL tumors are sub-classified into various subtypes primarily based on their distinct clinical differences. The three most common subtypes of PTCL are peripheral T-cell lymphoma not otherwise specified (PTCL-NOS), anaplastic large-cell lymphoma (ALCL), and angio-immunoblastic T-cell lymphoma (AITL). Each of these three subtypes is an aggressive cancer.

Treatment regimens generally comprise combination chemotherapy, such as CHOP (cyclophosphamide, doxorubicin, vincristine, prednisone), EPOCH (etoposide, vincristine, doxorubicin, cyclophosphamide, prednisone), or other multi-drug regimen. More recently approved treatments include belinostat, a histone deacetylase inhibitor for treatment of patients with relapsed or refractory PTCL; pralatrexate for treatment of patients with relapsed or refractory PTCL; and romidepsin for the treatment of PTCL in patients who have received at least one prior therapy. Most patients with PTCL will relapse.

Notch signaling is an evolutionary conserved pathway that plays an integral role in development and tissue homeostasis in mammals. The Notch receptors and ligands contain single-pass transmembrane domains, are expressed on the cell surface and, for that reason, Notch signaling is particularly important in mediating communication between adjacent cells expressing the receptors and ligands. There are four known Notch receptors found in rodents and humans, termed Notch 1 to Notch 4. The Notch receptors are heterodimeric proteins composed of extracellular and intracellular domains that are initially synthesized as a single polypeptide. Receptor-ligand interaction triggers a series of proteolytic cleavages of the Notch receptor polypeptide in which γ-secretase activity is involved. γ-Secretase activity cleaves Notch intracellular domain from the cell surface which translocates to the nucleus to form a transcription factor complex. Notch intracellular domain (NICD) is the active form of the protein. Various Notch signaling functions include proliferation, differentiation, apoptosis, angiogenesis, migration and self-renewal. These diverse roles of Notch signaling during the development and maintenance of normal tissues are aberrantly activated in different forms of cancer. The oncogenic functions of Notch signaling include the inhibition of apoptosis and the promotion of cell proliferation.

Recently, a specific Notch pathway signaling inhibitory compound having activity against various tumor types has been disclosed in WO 2013/016081.

There is a need for therapeutic agents that exhibit activity (efficacy) in the treatment of PTCL, particularly aggressive forms of PTCL. There is also a need for an alternative therapeutic agent to those combinations and individual therapeutic agents currently used to treat PTCL. The Notch inhibitor 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, is an alternative therapeutic agent and evidences surprising and unexpected therapeutic activity against PTCL, particularly aggressive forms of PTCL.

One aspect of the invention provides a method of treating a patient suffering from aggressive PTCL comprising administering to a PTCL-NOS, ALCL, or AITL patient in need of treatment an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof.

Another aspect of the invention provides a method of treating a patient suffering from aggressive PTCL comprising administering to a PTCL-NOS, ALCL, or AITL patient in need of treatment 25 to 75 mg/dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof.

A further aspect of the invention provides a method of treating a patient suffering from aggressive PTCL comprising administering to a PTCL-NOS, ALCL, or AITL patient in need of treatment 25 to 75 mg/dose three times per week over a seven day week of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof.

Another aspect of the invention provides a compound or a pharmaceutically acceptable salt or hydrate thereof for use in the treatment of aggressive PTCL which is PTCL-NOS, ALCL, or AITL, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof.

A further aspect of the invention provides a compound or a pharmaceutically acceptable salt or hydrate thereof for use in the treatment of aggressive PTCL which is PTCL-NOS, ALCL, or AITL, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof, administered at 25 to 75 mg/dose.

Another aspect of the invention provides a compound or a pharmaceutically acceptable salt or hydrate thereof for use in the treatment of aggressive PTCL which is PTCL-NOS, ALCL, or AITL, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof administered at 25 to 75 mg/dose three times per week over a seven day week.

A further aspect of the invention provides the use of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for preparation of a medicament for treatment of aggressive PTCL which is PTCL-NOS, ALCL, or AITL.

Another aspect of the present invention provides the use of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for preparation of a medicament for treatment of aggressive PTCL which is PTCL-NOS, ALCL, or AITL wherein said medicament is to be administered at a dose of 25 to 75 mg of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof.

A further aspect of the present invention provides the use of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for preparation of a medicament for treatment of aggressive PTCL which is PTCL-NOS, ALCL, or AITL wherein said medicament is to be administered three times per week over a seven day week at a dose of 25 to 75 mg of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof.

The compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide is taught to be a Notch inhibitor in WO 2013/016081. The name identifies a compound having the following structure:

Compound 1

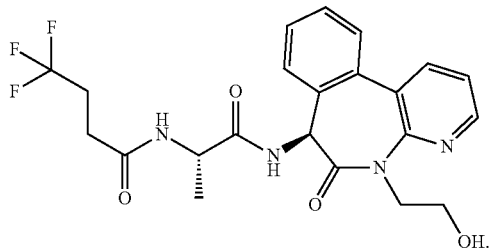

Compound 1 is named: 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide (IUPAC); and may also be named: N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluorobutanamide (CAS); and other names to unambiguously identify Compound 1.

It will be understood Compound 1 is depicted as a single stereoisomer. There are two chiral centers giving rise to four diastereomers. As used herein, references to Compound 1 are meant to also include racemic mixtures including Compound 1. Herein, the Cahn-Ingold-Prelog designations of (R)- and (S)- are used to refer to specific isomers. Specific stereoisomers can be prepared by stereospecific synthesis using enantiomerically pure or enriched starting materials. The specific stereoisomers of either starting materials, intermediates, or racemic mixtures including Compound 1 can be resolved by techniques well known in the art, such as those found in *Stereochemistry of Organic Compounds*, E. I. Eliel and S. H. Wilen (Wiley 1994) and *Enantiomers, Racemates, and Resolutions*, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. While all mixtures containing the compound of the present invention are contemplated within the present invention, the preferred embodiment is Compound 1.

It has also been found that Compound 1 exists as atropisomers, or specific conformers. In aqueous solutions, 8-9% of atropisomer 2 (minor atropisomer) is detected by $^1$H NMR and LC-MS in equilibrium with atropisomer 1 (major atropisomer) at ambient temperature after 24 hours. In organic solvents, at ambient temperature after 24 hours, approximately 1-2% of atropisomer 2 is detected by $^1$H NMR and LC-MS in equilibrium with atropisomer 1. Although detectable by $^1$H NMR and LC-MS analysis, atropisomer 2 is not isolable.

"Effective amount" means the dosage of Compound 1, or pharmaceutically acceptable salt or hydrate thereof, or pharmaceutical composition containing the compound, or pharmaceutically acceptable salt or hydrate thereof, necessary to inhibit Notch signaling in an aggressive PTCL patient, and either destroy the target cancer cells or slow or arrest the progression of the cancer in a patient. Dosages of Compound 1 or a pharmaceutically acceptable salt or hydrate thereof in an adult are in the range of 25 to 75 mg/dose. In a pediatric patient, dosages may be lower and are anticipated to be based on surface area. The exact dosage required to treat a patient and the length of treatment time will be determined by a physician in view of the age, stage and severity of the disease as well as the specific needs and response of the individual patient.

The administration regimen may be adjusted to provide a more optimal therapeutic benefit to a patient and to manage or ameliorate observed gastrointestinal toxicities such as diarrhea, nausea, vomiting, mucoid enteropathy (hypersecretion and accumulation of mucus in the gastrointestinal tract), and/or colitis, or symptoms related to tumor necrosis. Preferred administration is every other day over a five day period followed by two days without administration (T.I.W.) during a 28-day cycle. An alternative preferred administration regimen is to administer to a patient in need of treatment, a loading dose of: a) at least one dose and up to 12 doses; or b) at least one dose and up to 6 doses; or c) at least one dose and up to 3 doses, at 75-150 mg/dose administered twice or three times per week during a 28 day cycle; followed by a maintenance dose of 50 mg/dose administered three times per week; and optionally administering, during administration of the loading dose, 1-50 mg/day of a corticosteroid. At least one loading dose is administered and as many as 12 loading doses over one 28 day cycle are administered. Preferably, 1 to 6 loading doses are administered over 14 days of a 28 day cycle. Also preferably, at least one loading dose and up to 3 loading doses are administered over 7 days of a 28 day cycle. It will be appreciated the number of loading doses is dependent on whether the administration regimen is twice per week or three times per week. A maintenance or second dose of 50 mg per dose is administered TIW following the loading dose or doses. Preferably, the maintenance dose is administered over any remaining days of a first 28 day cycle to one or more additional 28 day cycles. The optional, administration (pre-, concomitant, or post-administration of Compound 1) of a corticosteroid, such as hydrocortisone, hydrocortisone acetate, cortisone acetate, tixocortol pivalate, prednisolone, methylprednisolone, prednisone, and dexamethasone is on an as needed basis to manage or ameliorate gastrointestinal toxicities including diarrhea, nausea, vomiting, mucoid enteropathy and/or colitis. Any or all of the dosage, administration regimen and cycle, may be modified at the discretion of a physician due to tumor necrosis or other factors.

The term "aggressive PTCL" and "aggressive peripheral T-cell lymphoma" means a solid tumor selected from peripheral T-cell lymphoma not otherwise specified (PTCL-NOS), anaplastic large-cell lymphoma (ALCL), and angioimmunoblastic T-cell lymphoma (AITL).

The terms "treatment," "treat," and "treating," are meant to include the full spectrum of intervention for the cancer from which the patient is suffering, such as administration of the active compound to alleviate, slow, or reverse one or more of the symptoms and to delay progression of the cancer even if the cancer is not actually eliminated. The patient to be treated is a mammal, in particular a human.

The compound of the present invention is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY, L. V. Allen, Editor, $22^{nd}$ Edition, Pharmaceutical Press, 2012). In a particular embodiment, the pharmaceutical composition comprises 4,4,4-trifluoro-N-[(1S)-2-[[(7S)-5-(2-hydroxyethyl)-6-oxo-7H-pyrido[2,3-d][3]benzoazepin-7-yl]amino]-1-methyl-2-oxo-ethyl]butanamide, or a pharmaceutically acceptable salt or hydrate thereof, and a pharmaceutically acceptable carrier. The present invention also provides pharmaceutical compositions comprising 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof with a pharmaceutically acceptable carrier and optionally one or more other therapeutic agents.

The compound of the present invention is capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

Compound 1, or a pharmaceutically acceptable salt or hydrate thereof, may be prepared by a variety of procedures known in the art, as well as those described in WO2013/016081. The specific synthetic steps may be combined in different ways to prepare Compound 1, or a pharmaceutically acceptable salt or hydrate thereof.

The compounds employed as initial starting materials in the synthesis of the compound of the present invention are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, $5^{th}$ Edition, Michael B. Smith and Jerry March, Wiley Interscience, 2001; Advanced Organic Chemistry, $4^{th}$ Edition, Part B, Reactions and Synthesis, Francis A. Carey and Richard J. Sundberg, Kluwer Academic/Plenum Publishers, 2000, etc., and references cited therein.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

PET/CT imaging of cancer with combined positron emission tomography (PET) and X-ray computerized tomography (CT) scanners has become a standard component of diagnosis and staging in oncology. The use of the radiolabeled tracer 2-deoxy-2-[$^{18}$F]fluoro-D-glucose (FDG) is used for the majority of all PET/CT imaging procedures. One of the advantages of PET/CT imaging is its ability to detect, very early during treatment, significant changes in glucose metabolism or even complete shutoff of the neoplastic cell metabolism as a surrogate of tumor chemosensitivity assessment. In addition to cancer detection and staging, PET/CT imaging is becoming increasingly important as a quantitative monitor of individual response to therapy and an evaluation tool for new drug therapies. Changes in FDG accumulation have been shown to be useful as an imaging marker for assessing response to therapy. RECIST criteria, where response of tumors to therapy has traditionally assessed by measurement of changes in size/dimension of the tumors in CT images may not evidence early response to the therapy. Changes in size of tumors as a result of therapy may take a long period of time to develop. The most widely used parameter is the standardized uptake value (SUV) is defined as the maximal SUV value ($SUV_{MAX}$) in the region of interest and reduction in $SUV_{MAX}$ is generally considered the most reliable indicator of the metabolic activity shutdown.

The oncogenic role of Notch was first reported in human T-cell leukemia involving a translocation of the Notch1 intracellular domain to the T-cell receptor-β promoter region, resulting in the over expression of Notch1 intracellular domain (Grabher et al. *Nature Review Cancer,* 2006 (6):347-359; Weng et al. *Science,* 2004(306):269-271). Over expression of Notch1 intracellular domain in hematopoietic progenitor cells of mice caused the mice to exhibit T-cell acute lymphoblastic leukemia similar to humans. In addition to T-cell acute lymphoblastic leukemia, there is increasing evidence that Notch signals are oncogenic in other cancers through multiple mechanisms including acute lymphoblastic leukemia, acute myelogenous leukemia, chronic myelogenous leukemia and erythroleukemia.

As noted above, peripheral T-cell lymphoma (non-Hodgkin lymphoma) is a solid tumor cancer of the lymphatic system that develops from mature T-lymphocytes (T-cells). This is in contrast to leukemia, T-cell acute lymphoblastic leukemia, acute lymphoblastic leukemia, acute myelogenous leukemia, chronic myelogenous leukemia, and erythroleukemia that are all cancers of immature blood-forming cells. Leukemia starts in the bone marrow and the cancerous cells spread from there into the bloodstream and to other parts of the body. The leukemia is described as lymphoid or myeloid, depending on which progenitor blood-forming cell in the maturation cascade the leukemia cells develop from.

Aberrant constitutive Notch signaling is also implicated in a number of solid tumor malignancies including breast cancer, ovarian cancer (Park et al. *Cancer Research,* 2006 (66):6312-6318), melanoma (Gast et al. *Genes, Chromosomes & Cancer,* 2010(49):733-745), lung cancer, non-small cell lung cancer (Westhoff et al. PNAS, 2009(106):22293-22298), pancreatic cancer, glioblastoma, colorectal cancer, head and neck cancer, cervical cancer, prostate cancer, liver cancer, squamous cell carcinoma (oral), skin cancer and medulloblastoma (Ranganathan et al., *Nature Review Cancer,* 2011(11):338-351 and Supplementary Information S1 (table)). Aberrant Notch signaling may be activated in particular soft tissue sarcomas Guijarro et al. *Am J Pathol,* 2013 (182(6)):2015-2027.

Inhibition of Notch signaling presents an attractive target to provide therapeutic benefits to cancer patients whose disease was induced, maintained and progressed, or exacerbated by aberrant activation of the constitutive Notch signaling pathway. Shih et al. *Cancer Research,* 2007 (67) 1879-1882.

Ex Vivo Assay

An immunohistochemistry (IHC) assay is carried out using a PT Link, a Dako Autostainer Link 48, and Leica ST5020 Linear Stainer to analyze Notch 1, 2, and 3 intracellular domains (N1ICD, N2ICD, and N3ICD, respectively) expression by an Antibody Panel Method in human tumor samples.

TABLE 1

| Reagent Name | Source | Catalogue/ Identification | Composition and Concentration |
| --- | --- | --- | --- |
| EnVision ™ FLEX + Rabbit (LINKER) | Dako | K8009/SM805 | Ready to Use |
| EnVision ™ FLEX/HRP | Dako | K8000/SM802 | Dextran coupled with peroxidase molecules and goat secondary antibody molecules against rabbit and mouse immunoglobulins. Ready to Use |
| EnVision ™ FLEX Peroxidase - Blocking Reagent | Dako | K8000/SM801 | Phosphate buffer containing hydrogen peroxide, 15 mmol/L NaN3 and detergent. Ready to Use |
| EnVision ™ FLEX Substrate Buffer | Dako | K8000/SM803 | Buffered solution containing hydrogen peroxide and preservative. Ready to Use |
| EnVision ™ FLEX DAB + Chromogen | Dako | K8000/SM827 | 3,3'-diaminobenzidine tetrahydrochloride in organic solvent. Ready to Use |
| EnVision ™ FLEX Wash Buffer (20x) | Dako | K8007/DM831 | Tris-buffered saline solution containing Tween ® 20, pH 7.6 (±0.1); 20x concentration; diluted to a 1x use concentration with Milli-Q ® DI (deionized) water (EMD Millipore). |
| Dako Antibody Diluent | Dako | S0809 | Tris-HCl buffer containing stabilizing protein and 0.015 mol/L sodium azide. Ready to Use |

TABLE 1-continued

| Reagent Name | Source | Catalogue/ Identification | Composition and Concentration |
| --- | --- | --- | --- |
| EnVision ™ FLEX Target Retrieval Solution, High pH (50x) | Dako | K8000/DM828 | Citrate buffer, pH 9.0; 50x concentration; diluted to a 1x use concentration with Milli-Q ® water (EMD Millipore), pH 8.9-9.1. |
| FLEX Rabbit Negative Control, Ready-to-Use | Dako | Catalogue only: IR600 | Immunoglobulin fraction of serum from non-immunized rabbits, solid phase absorbed. Ready to Use |
| EnVision ™ FLEX Hematoxylin | Dako | K8008/SM806 | Modified Mayer's Hematoxylin. Ready to Use |

Patient tumor specimens are collected by techniques known and routinely used by those skilled in the art. The specimens are formalin-fixed, paraffin embedded (FFPE) biospecimens (blocks and/or slides), prepared at the time of collection.

Each of Notch 1 ICD antibody, Notch 2 ICD antibody, and Notch 3 ICD antibody, used in this assay are from proprietary hybridomas created in rabbits using human antigens from the respective cleavage site. Suitable Notch 1 ICD, Notch 2 ICD, and Notch 3 ICD antibodies against human forms of each Notch ICD are commercially available from various entities (Biocompare; The Buyer's Guide for Life Sciences). A suitable immunohistochemistry assay for detecting Notch 1, 2, and 3 intracellular domains (ICD) expression in human tissue samples may be prepared using the commercially available antibodies.

The full length amino acid sequence for human Notch 1 preprotein is found at the National Center for Biotechnology Information (NCBI) Reference Sequence: NP_060087.3; human Notch 2 preprotein, NCBI Reference sequence: AAA36377.2; and human Notch 3 preprotein, NCBI Reference Sequence: NP_000426.2. The Notch 1 ICD amino acid sequence is found at UniProt, reference P46531 (neurogenic locus notch homolog protein 1); Notch 2 ICD amino acid sequence is found at UniProt, reference Q04721 (neurogenic locus notch homolog protein 2); and Notch 3 ICD amino acid sequence is found at UniProt, reference Q9UM47 (neurogenic locus notch homolog protein 3).

The Notch 1 ICD antibody is a monoclonal rabbit antibody that binds to the gamma-secretase cleaved human Notch 1 intracellular domain, Val 1754 through 2555, reactome.org identifier: R-HSA-157634. The Notch 2 ICD antibody is a monoclonal rabbit antibody that binds to the gamma-secretase cleaved human Notch 2 intracellular domain, Val 1697-2471, reactome.org identifier: R-HSA-157942. The Notch 3 ICD antibody is a monoclonal rabbit antibody that binds to the gamma-secretase cleaved human Notch 3 intracellular domain, Val 1662-2321, reactome.org identifier: R-HSA-157647. The Notch 1 ICD antibody working concentration of 1.5 µg/ml is prepared by admixing with Dako Antibody Diluent (Dako; S0809. For each of Notch 2 ICD antibody and Notch 3 ICD antibody, a working concentration of 2.0 µg/ml is prepared by admixing with Dako Antibody Diluent (Dako; S0809).

A 1× wash buffer solution is prepared by admixing EnVision™FLEX Wash Buffer (Dako catalogue K8007, ID number DM831) and Milli-Q® DI (deionized) water (EMD Millipore).

A 1× target retrieval solution, high pH, is prepared by admixing Milli-Q® water (EMD Millipore) and EnVision™ FLEX Target Retrieval Solution, high pH (Dako catalogue K8000, ID number DM828) to afford a solution of pH 8.9-9.1.

A substrate working solution is prepared by admixing EnVision™Flex substrate buffer (Dako, catalogue number K8000, ID number SM803) and 1 (one) drop of EnVision™ FLEX DAB+Chromagen (Dako, catalogue number K8000, ID number SM827) per mL of EnVision™ Flex substrate buffer.

An appropriate volume of FLEX Rabbit negative control, ready to use reagent (Dako, catalogue number IR600) is used.

Unstained slides are prepared, if not provided in useable form, from FFPE block biospecimens. Appropriate reagents and slides are loaded in the Dako PT Link and then the Dako Autostainer Link 48 following the manufacturer's instructions for each. Results from this assay are provided below in Table 2.

TABLE 2

| | Diagnosis | Slide Identification | Stain | Results |
|---|---|---|---|---|
| 1 | AITL | AITL1-1 | Notch 1 | Positive |
| 2 | AITL | AITL1-2 | Notch 2 | Negative |
| 3 | AITL | AITL1-3 | Notch 3 | Negative |
| 4 | AITL | AITL1-4 | Negative Control | Negative |
| 5 | AITL | AITL2-1 | Notch 1 | Positive |
| 6 | AITL | AITL2-2 | Notch 2 | Negative |
| 7 | AITL | AITL2-3 | Notch 3 | Negative |
| 8 | AITL | AITL2-4 | Negative Control | Negative |
| 9 | AITL | AITL3-1 | Notch 1 | Positive |
| 10 | AITL | AITL3-2 | Notch 2 | Negative |
| 11 | AITL | AITL3-3 | Notch 3 | Negative |
| 12 | AITL | AITL3-4 | Negative Control | Negative |
| 13 | AITL | AITL4-1 | Notch 1 | Positive |
| 14 | AITL | AITL4-2 | Notch 2 | Negative |
| 15 | AITL | AITL4-3 | Notch 3 | Negative |
| 16 | AITL | AITL4-4 | Negative Control | Negative |
| 17 | AITL | AITL5-1 | Notch 1 | Positive |
| 18 | AITL | AITL5-2 | Notch 2 | Negative |
| 19 | AITL | AITL5-3 | Notch 3 | Negative |
| 20 | AITL | AITL5-4 | Negative Control | Negative |
| 21 | AITL | AITL6-1 | Notch 1 | Positive |
| 22 | AITL | AITL6-2 | Notch 2 | Negative |
| 23 | AITL | AITL6-3 | Notch 3 | Negative |
| 24 | AITL | AITL6-4 | Negative Control | Negative |
| 25 | AITL | AITL7-1 | Notch 1 | Positive |
| 26 | AITL | AITL7-2 | Notch 2 | Negative |
| 27 | AITL | AITL7-3 | Notch 3 | Negative |
| 28 | AITL | AITL7-4 | Negative Control | Negative |
| 29 | AITL | AITL8-1 | Notch 1 | Positive |
| 30 | AITL | AITL8-2 | Notch 2 | Negative |
| 31 | AITL | AITL8-3 | Notch 3 | Negative |
| 32 | AITL | AITL8-4 | Negative Control | Negative |
| 33 | AITL | AITL9-1 | Notch 1 | Positive |
| 34 | AITL | AITL9-2 | Notch 2 | Negative |
| 35 | AITL | AITL9-3 | Notch 3 | Negative |
| 36 | AITL | AITL9-4 | Negative Control | Negative |
| 37 | AITL | AITL10-1 | Notch 1 | Positive |
| 38 | AITL | AITL10-2 | Notch 2 | Negative |
| 39 | AITL | AITL10-3 | Notch 3 | Negative |
| 40 | AITL | AITL10-4 | Negative Control | Negative |
| 41 | AITL | AITL11-1 | Notch 1 | Positive |
| 42 | AITL | AITL11-2 | Notch 2 | Negative |
| 43 | AITL | AITL11-3 | Notch 3 | Negative |
| 44 | AITL | AITL11-4 | Negative Control | Negative |
| Positive Control | | | Notch 1 | Positive |
| Positive Control | | | Notch 2 | Positive |
| Positive Control | | | Notch 3 | Positive |
| 45 | AITL | AITL12-1 | Notch 1 | Positive |
| 46 | AITL | AITL12-2 | Notch 2 | Negative |
| 47 | AITL | AITL12-3 | Notch 3 | Negative |
| 48 | AITL | AITL12-4 | Negative Control | Negative |
| 49 | AITL | AITL13-1 | Notch 1 | Positive |
| 50 | AITL | AITL13-2 | Notch 2 | Negative |
| 51 | AITL | AITL13-3 | Notch 3 | Negative |
| 52 | AITL | AITL13-4 | Negative Control | Negative |
| 53 | AITL | AITL14-1 | Notch 1 | Positive |
| 54 | AITL | AITL14-2 | Notch 2 | Negative |
| 55 | AITL | AITL14-3 | Notch 3 | Negative |
| 56 | AITL | AITL14-4 | Negative Control | Negative |
| 57 | AITL | AITL15-1 | Notch 1 | Positive |
| 58 | AITL | AITL15-2 | Notch 2 | Negative |
| 59 | AITL | AITL15-3 | Notch 3 | Negative |
| 60 | AITL | AITL15-4 | Negative Control | Negative |
| 61 | AITL | AITL16-1 | Notch 1 | Positive |
| 62 | AITL | AITL16-2 | Notch 2 | Negative |
| 63 | AITL | AITL16-3 | Notch 3 | Negative |
| 64 | AITL | AITL16-4 | Negative Control | Negative |
| 65 | AITL | AITL17-1 | Notch 1 | Negative |
| 66 | AITL | AITL17-2 | Notch 2 | Negative |
| 67 | AITL | AITL17-3 | Notch 3 | Negative |
| 68 | AITL | AITL17-4 | Negative Control | Negative |
| 69 | AITL | AITL18-1 | Notch 1 | Positive |
| 70 | AITL | AITL18-2 | Notch 2 | Negative |
| 71 | AITL | AITL18-3 | Notch 3 | Negative |
| 72 | AITL | AITL18-4 | Negative Control | Negative |
| 73 | AITL | AITL19-1 | Notch 1 | Positive |
| 74 | AITL | AITL19-2 | Notch 2 | Negative |
| 75 | AITL | AITL19-3 | Notch 3 | Negative |
| 76 | AITL | AITL19-4 | Negative Control | Negative |
| 77 | AITL | TLN14-007-007 | Notch 1 | Positive |
| 78 | AITL | TLN14-007-008 | Notch 2 | Negative |
| 79 | AITL | TLN14-007-009 | Notch 3 | Negative |
| 80 | AITL | TLN14-007-010 | Negative Control | Negative |
| Positive Control | | | Notch 1 | Positive |
| Positive Control | | | Notch 2 | Positive |
| Positive Control | | | Notch 3 | Positive |

The data in Table 2 shows Notch 1 ICD, and as a consequence, Notch pathway signaling, is upregulated in AITL human patient tumor samples in this assay. These data, from this assay, suggest a Notch 1 pathway signaling inhibitor, such as 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, will demonstrate efficacy against aggressive PTCL tumors.

Clinical Evaluation

A study of 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in patients with advanced or metastatic cancer.

Study Design

This study is a multicenter, nonrandomized, open-label, dose-escalation study followed by cohort expansion of oral dosed 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in outpatients with advanced or metastatic cancer.

Study Objectives

The primary objective of this study is to determine a recommended Phase 2 dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate that may be safely administered to patients with advanced or metastatic cancer. The primary objective is to confirm the recommended Phase 2 dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate that may be safely administered to patients with specific tumor types and to document antitumor activity.

The secondary objectives of the study are to characterize the safety and toxicity profile of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate as assessed by National Cancer Institute's (NCI) Common Terminology Criteria for Adverse Events (CTCAE) v 4.0; to estimate the pharmacokinetic (PK) parameters of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate; to document any antitumor activity observed with 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate; and to assess duration of response, progression-free survival (PFS), and overall survival (OS).

Exploratory objectives are to explore renal clearance and PK metabolites of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in plasma and urine; explore predictive biomarkers related to 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate; explore pharmacodynamic (PD) effects of 4,4,4-trifluoro-N-[(1S)-2-[[(7S)-5-(2-hydroxyethyl)-6-oxo-7H-pyrido[2,3-d][3]benzazepin-7-yl]]-1-methyl-2-oxo-ethyl]butanamide hydrate on biomarkers indicative of Notch activity (Notch intracellular domain by immunohistochemistry or an alternative validated method) including cytokeratin 18 or Rules Based Medicine; explore the utility of positron emission tomography (PET) scan or PET/computed tomography (CT), PET/CT, to assess treatment effect with 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate; and to explore the utility of dynamic contrast enhanced magnetic resonance imaging (DCE-MRI) to assess treatment effect with 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate.

Study Design

Cohort expansion of oral 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in outpatients with advanced or metastatic cancer. Patients will be entered based on screened molecular alterations related to the Notch pathway. Patients initially dosed with 75 mg/dose administered T.I.W. are dose-reduced to 50 mg/dose administered T.I.W.

Trial Drug 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate, given orally as capsules 3 times per week during a 28-day cycle.

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate will be supplied as 25 and 50 mg capsules in bottles for oral consumption. These capsules should be stored at room temperature within the temperature range stated on the label.

Planned Duration of Treatment

Patients will receive 2 cycles (28 days each) of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate unless one or more of the criteria for discontinuation are fulfilled. A patient may receive more than 2 cycles of treatment only if: 1) none of the criteria for discontinuation have been fulfilled, and 2) the investigator determines that the patient is experiencing clinical benefit from the treatment.

The planned duration is not fixed; patients will remain on study until they fulfill one (1) of the criteria for study discontinuation. The post-discontinuation follow-up period begins the day after the patient and the investigator agree that the patient will no longer continue study treatment and is defined by the following periods:

The short term follow-up period begins 1 day after discontinuation of study treatment and lasts approximately 30 days.

The long-term follow-up period begins 1 day after the short-term follow-up period is completed and continues until death or study closure to collect survival data.

After discontinuation, tumor measurements and other study procedures will be performed.

This study will be considered closed approximately 12 months from the date that the last patient was enrolled. Patients who are benefiting from treatment may continue to receive study drug for long-term durations, even after the study has closed and final database lock has occurred in the continued access period.

Dosing 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate will be administered orally TIW following one of the following schedules (decision at investigator's discretion):

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate will be administered orally TIW following 1 of these schedules (decision at investigator's discretion):

Monday, Wednesday, Friday every week for a 28-day cycle;

Tuesday, Thursday, Saturday every week for a 28-day cycle;

Wednesday, Friday, Sunday every week for a 28-day cycle;

Thursday, Saturday, Monday every week for a 28-day cycle.

Criteria for Evaluation

Safety: NCI CTCAE, version 4.0, adverse events (AE) and dose-limiting toxicities (DLT); collection of blood and urine samples for standard laboratory tests, including chemistry, hematology, coagulation, and urinalysis.

Bioanalytical (including PK and PD): Plasma concentrations of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate.

Efficacy: Efficacy will be assessed using Response Evaluation Criteria in Solid Tumors (RECIST) v1.1 or using the Cheson et al., *J. Clin. Oncol.*, 2007, 25(5): 579-586, response criteria for lymphoma. Each patient will be assessed by 1 or more of the following radiologic tests for tumor measurement: X-ray computerized tomography (CT) scan; magnetic resonance imaging (MRI); chest X-ray; positron emission tomography (PET) scan; dynamic contrast enhanced-magnetic resonance imaging (DCE-MRI); PET/CT imaging Standardized Uptake Values ($SUV_{MAX}$); Dynamic Contrast-Enhanced Ultrasonography (DCE-US).

Each patient's full extent of disease will also be assessed with: applicable tumor measurement by RECIST 1.1 (Eisenhauer et al., *Eur J Cancer.* 2009, 45(2): 228-247); Cheson et al., *J. Clin. Oncol.*, 2007, 25(5): 579-586; and Choi et al., *J Clin Oncol.* 2007, 25(13): 1753-1759; and evaluation of performance status by ECOG, Oken et al., *Am J Clin Oncol.* 1982, 5: 649-655. To confirm objective responses, all lesions should be radiologically assessed, and the same radiologic method used for the initial response determination should be repeated at least 4 weeks following the initial observation of an objective response, using the sample method that was used at baseline. Partial metabolic response by PET scan is defined as a minimum of 15±25% in tumor [18F]-FDG SUV after one cycle of therapy, and greater than 25% after more than one treatment cycle and should be confirmed at least 4 weeks later, according to PET response criteria of the European Organization for Research and Treatment of Cancer (Young et al., *Eur J Cancer,* 1999, December, 35(13): 1773-82.

Statistical Methods

Safety: Dose escalation will be driven by safety using the 3+3 method. Model-based analyses that incorporate prior expectations about the dose-toxicity curve will be fitted to the data at the end of each cohort, which will be used by investigators and Lilly clinical research physician to determine the next dose level. The maximum tolerated dose is defined as the highest tested dose that has less than 33% probability of causing a DLT during Cycle 1.

Efficacy: Tumor response data will be tabulated and summarized by study part.

Pharmacokinetics: PK parameters for 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate will be analyzed by standard non-compartmental methods of analysis.

Pharmacodynamics: All PD data will be assessed. Exploratory PK/PD analyses may be conducted to identify the exposure-biomarker response relationship.

Exploratory Samples:

Blood samples will be collected for exploratory analysis of circulating Amyloid beta (Aβ) peptides before and after treatment.

Where local regulations allow, a blood sample will be collected for pharmacogenetic (PGx) analysis. It is a 1-time collection.

Samples will be stored and exploratory analysis may be performed to identify genetic variants that might play a role in tumor biology or to evaluate their association with observed clinical outcomes to 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide.

These investigations may be limited to a focused candidate gene study or, if appropriate, genome wide association studies may be performed to identify regions of the genome associated with the variability observed in drug response. Samples will only be used for investigations related to disease and drug or class of drugs under study in the context of this clinical program. They will not be used for broad exploratory unspecified disease or population genetic analysis.

In the event of an unexpected AE or the observation of unusual response, the samples may be genotyped and analysis may be performed to evaluate a genetic association with response to A mandatory tumor tissue sample and a skin punch sample obtained previously, within two years of the date of enrollment, or a fresh sample if no archival sample can be located for measuring various biomarkers, potentially including gene-expression profiling as well as other exploratory biomarkers. Pre- and post-dose tumor and skin biopsies will also be collected for analysis.

Preliminary data on 3 patients having relapsed or refractory peripheral T-Cell lymphoma (two with AITL and one with PTCL-NOS administered 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in cycle 1 of an ongoing clinical trial are presented in Table 3.

TABLE 3

| Patient | Tumor type | CT Scan assessment | PET Scan | Other assessments |
|---|---|---|---|---|
| 1 | AITL | Tumor decrease of 80% | Partial response | |
| 2 | AITL | Tumor decrease of 20% | — | |
| 3 | PTCL-NOS | Stable | | Decrease of Abnormal T cells and hematological recovery of platelets |

We claim:

1. A method of treating a patient suffering from aggressive peripheral T-cell lymphoma (PTCL), comprising administering to a PTCL not otherwise specified (PTCL-NOS), anaplastic large-cell lymphoma (ALCL), or angioimmunoblastic T-cell lymphoma (AITL) patient in need of treatment an effective amount of 4,4,4-trifluoro-N-[(1S)-2-[[(7S)-5-(2-hydroxyethyl)-6-oxo-7H-pyrido[2,3-d] [3]benzazepin-7-yl]amino]-1-methyl-2-oxo-ethyl]butanamide, or a pharmaceutically acceptable salt or hydrate thereof, wherein the administering comprises:
administering a loading dose of 75 mg/dose of 4,4,4-trifluoro-N-[(1S)-2-[[(7S)-5-(2-hydroxyethyl)-6-oxo-7H-pyrido[2,3-d] [3]benzazepin-7-yl]amino]-1-methyl-2-oxo-ethyl]butanamide or a pharmaceutically acceptable salt or hydrate thereof two or three times per week for at least one week of a 28 day cycle; followed by
administering a maintenance dose of 50 mg/dose of 4,4,4-trifluoro-N-[(1S)-2-[[(7S)-5-(2-hydroxyethyl)-6-oxo-7H-pyrido[2,3-d] [3]benzazepin-7-yl]amino]-1-methyl-2-oxo-ethyl]butanamide or a pharmaceutically acceptable salt or hydrate thereof three times per week.

2. The method of claim 1, wherein the loading dose of 4,4,4-trifluoro-N-[(1S)-2-[[(7S)-5-(2-hydroxyethyl)-6-oxo-7H-pyrido[2,3-d] [3]benzazepin-7-yl]amino]-1-methyl-2-oxo-ethyl]butanamide or a pharmaceutically acceptable salt or hydrate thereof is administered every other day over a five day period followed by two days without administration (T.I.W.).

3. The method of claim 1, wherein the maintenance dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof is administered T.I.W.

4. The method of claim 1, wherein:
2 or 3 loading doses are administered over the course of one week;
4 to 6 loading doses are administered over the course of two weeks; or
8 to 12 loading doses are administered over the course of four weeks.

5. The method of claim 1, wherein the administration is oral.

6. The method of claim 1, wherein the patient has advanced or metastatic PTCL-NOS, ALCL, or AITL.

7. The method of claim 1, wherein the maintenance dose is administered over any remaining days of the 28 day cycle.

8. The method of claim 7, wherein, after the maintenance dose is administered over any remaining days of the 28 day cycle, the maintenance dose is administered over one or more additional 28 day cycles.

9. The method of claim 1, further comprising administering 1 to 50 mg/dose of a corticosteroid during administration of the loading dose.

10. The method of claim 9, wherein the corticosteroid is selected from the group consisting of hydrocortisone, hydrocortisone acetate, cortisone acetate, tixocortol pivalate, prednisone, methylprednisolone, and dexamethasone.

11. The method of claim 8, wherein:
2 or 3 loading doses are administered over the course of one week;
4 to 6 loading doses are administered over the course of two weeks; or
8 to 12 loading doses are administered over the course of four weeks.

12. The method of claim 1, wherein:
2 or 3 loading doses are administered over the course of one week; or
4 to 6 loading doses are administered over the course of two weeks; or
8 to 12 loading doses are administered over the course of four weeks; and
the maintenance dose is administered three times per week.

13. The method of claim 12, further comprising administering 1 to 50 mg/dose of a corticosteroid during administration of the loading dose.

14. The method of claim 13, wherein the corticosteroid is selected from the group consisting of hydrocortisone, hydrocortisone acetate, cortisone acetate, tixocortol pivalate, prednisone, methylprednisolone, and dexamethasone.

* * * * *